United States Patent [19]
Grabon

[11] Patent Number: 5,303,557
[45] Date of Patent: Apr. 19, 1994

[54] METHOD AND APPARATUS FOR DETERMINING THE PHASE OF A FLUID

[75] Inventor: Michel Grabon, Villeurbanne, France

[73] Assignee: Carrier Corporation, Syracuse, N.Y.

[21] Appl. No.: 89,928

[22] Filed: Jul. 12, 1993

[30] Foreign Application Priority Data

Aug. 10, 1992 [FR] France .................... 92 09873

[51] Int. Cl.$^5$ .................................... F17C 13/02
[52] U.S. Cl. ........................ 62/49.1; 62/129; 73/295; 137/392; 141/4
[58] Field of Search ............ 62/49.1, 49.2, 129; 73/295; 137/392; 141/4

[56] References Cited

U.S. PATENT DOCUMENTS

| | | | |
|---|---|---|---|
| 2,645,907 | 7/1953 | Droste et al. | 62/1 |
| 3,024,760 | 3/1962 | Enrico | 116/109 |
| 3,031,887 | 5/1962 | Weisend | 73/295 |
| 3,049,887 | 8/1962 | Sharp et al. | 62/49.2 |
| 3,262,280 | 7/1966 | Chaney | 62/49.2 |
| 3,456,490 | 7/1969 | Stone | 73/15 |
| 3,696,675 | 10/1972 | Gilmour | 73/295 |
| 3,914,950 | 10/1975 | Fletcher | 62/49.2 |
| 3,938,347 | 2/1971 | Riedel | 65/55 |
| 4,062,223 | 12/1977 | Lamphere et al. | 62/49.2 |
| 4,192,147 | 3/1980 | Gilbert et al. | 73/295 |
| 4,334,410 | 6/1982 | Drumare et al. | 62/49 |
| 4,409,809 | 9/1983 | Johnson et al. | 62/49 |

OTHER PUBLICATIONS

L. N. Dzhavadov and Yu I. Krotov, Measurement of $(\partial T/\partial P)_s$ for Solids and Liquids under Pressure to 36Pa, 3 Pribory i Tekhnika Eksperimenta 168–171 (May–Jun., 1985).

*Primary Examiner*—Ronald Capossela

[57] ABSTRACT

A method and apparatus for determining whether a fluid, such as a refrigerant, is a liquid or a gas. To determine whether the fluid at a predetermined level (14) of a storage container (20) is a liquid or a gas, fluid is withdrawn from the container at the predetermined level, depressurized under conditions that would cause it to become a gas if it is a liquid before such depressurization, then the temperature of the fluid after depressurization is measured and compared to a reference temperature that is or is related to the temperature of the fluid in the container. If the temperature of the fluid after depressurization and the reference temperature are approximately equal, one can conclude that the fluid withdrawn from the predetermined level is a gas. If the temperature of the fluid after depressurization is considerably lower than the reference temperature, one can conclude that the fluid withdrawn from the predetermined level is a liquid. Such a determination can be used, for example, in order to shut down an apparatus (3) for transferring a refrigerant into a receiving container when the liquid level in the container reaches a predetermined maximum level.

14 Claims, 2 Drawing Sheets

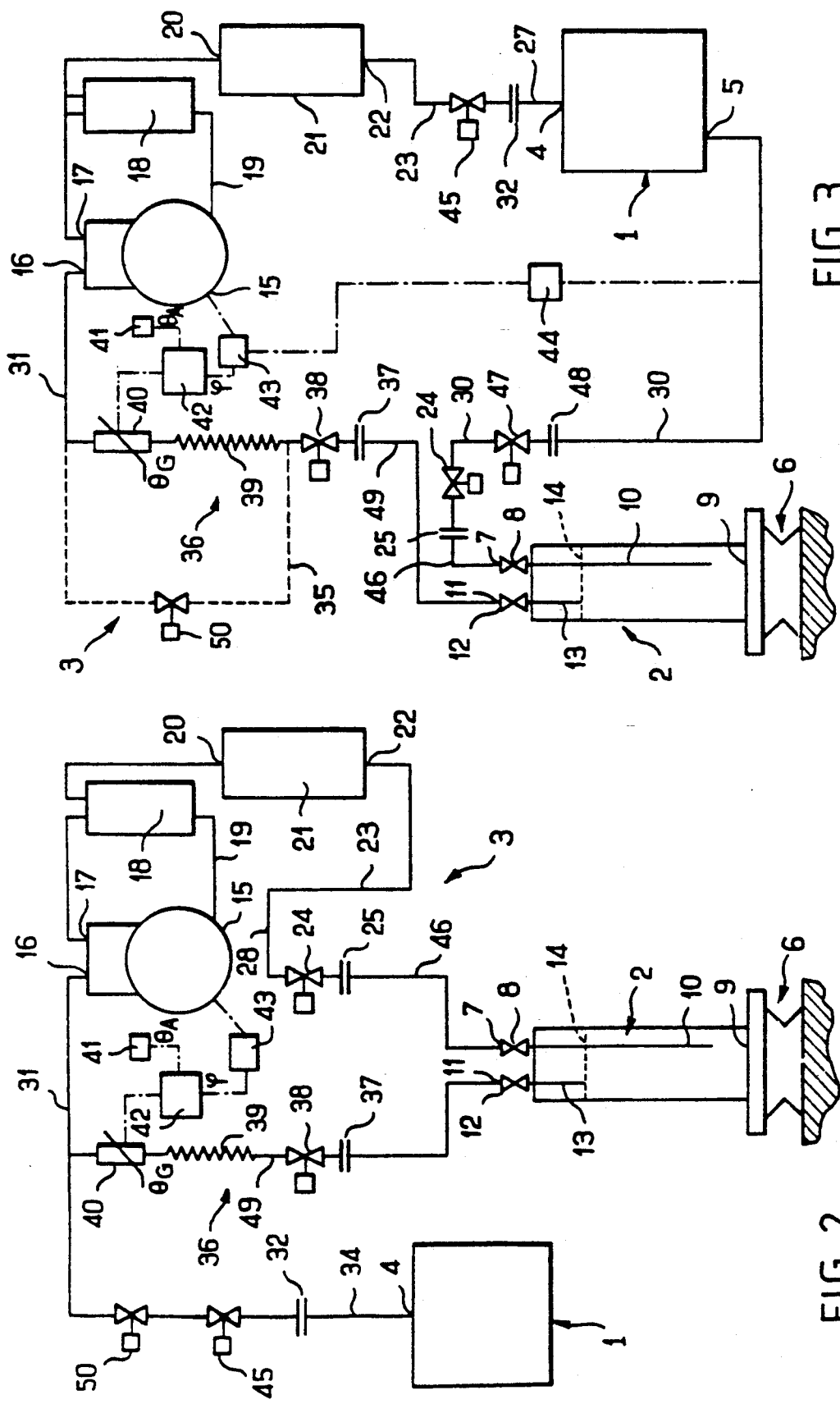

METHOD AND APPARATUS FOR DETERMINING THE PHASE OF A FLUID

BACKGROUND OF THE INVENTION

The present invention relates to a method and apparatus for determining the phase (i.e. liquid or gas) of a fluid at a certain level of a container, as well as a method and apparatus for transferring a fluid from a source container into a receiving container using such a method and apparatus.

It is often necessary to determine the level of fill in a fluid container, for example during the process of filling the container, in order not to exceed a predetermined maximum fill level, in order to avoid excessive pressure in the container or, when the fluid in the container is used, in order to determine that the fill level of the container has dropped below a minimum predetermined level, i.e., to detect the imminence of the container becoming empty.

For this purpose, the level at which the transition between the liquid and the gaseous phase of the fluid is located can be detected, but currently such detection can only be done visually through the walls of the container when these walls are transparent, which is only feasible for low-volume containers, such as cigarette lighters.

When the walls of the container are opaque, which is the most frequent case, particularly when the container has a large volume, for example, on the order of one or more liters, visual detection is not possible and then usually the container is weighed with its contents. However, this method is relatively inaccurate, while, when filling a pressurized gas cylinder, a certain safety margin must be provided regarding the fill level of the said enclosure as detected by weighing, in order to avoid excessive filling. Furthermore, this method has the disadvantage of requiring the use of weighing means.

SUMMARY OF THE INVENTION

One object of the present invention is to remedy this disadvantage. For this purpose, the present invention provides a method for determining the phase of a fluid at a certain level in a container by sampling the fluid in the container at that level, depressurizing the fluid under conditions that will cause the change of the fluid to a gas if it is a liquid before depressurization, measuring the temperature $\theta_G$ of the fluid after depressurization and determining a reference temperature $\theta_A$ as a function of the temperature of the fluid in the container, comparing the temperatures $\theta_G$ and $\theta_A$ and deducing the following from this comparison that either the temperature $\theta_G$ of the fluid after depressurization and the temperature of the fluid in the container are approximately equal, allowing the conclusion that the fluid at the certain level is a gas or the temperature $\theta_G$ after depressurization is considerably lower than the temperature of the fluid in the container, allowing the conclusion that the gas at the certain level is present in a liquid.

The present invention also includes an apparatus to implement the method characterized in that the apparatus comprises means for sampling the fluid in the container at a certain level and depressurizing the fluid thus sampled under conditions that will cause the fluid to change to a gas if it is a liquid before depressurization, means for measuring the temperature $\theta_G$ of the fluid after depressurization and means for measuring the reference temperature $\theta_A$ as a function of the temperature of the fluid in the container and means for comparing the temperatures $\theta_G$ and $\theta_A$ and producing a signal characteristic of the result of this comparison.

Thus, the invention is based on the fact that, when a fluid is subjected to depressurization, it will undergo a much smaller temperature reduction if it is initially a gas than if the depressurization results in a change of phase from liquid to gas. One can interpret a relatively large temperature change as being unambiguously characteristic of such a change in phase.

In this respect, one can choose to determine the reference temperature $\theta_A$ by measuring the temperature of the fluid in the container or by measuring the ambient temperature, which can normally be considered representative of the fluid in the container, these two temperatures normally being approximately the same as long as the fluid is not subjected to drastic temperature changes in the container, or by establishing a reference temperature that is lower than any probable value of the temperature of the fluid in the container, any drop below which by the temperature of the fluid after depressurization can be considered without ambiguity by one skilled in the art as evidence of the depressurization of a fluid that was initially a liquid, considering the operating conditions. The apparatus has means necessary for accomplishing these functions.

Of course, the fluid in the container can be sampled at a low flow rate i.e., comparable to that of a leak, without affecting the behavior of the fluid in the container or hindering its use in a traditional installation for fluid filling or use.

It can be easily seen that by using this invention a drop in the level of the surface of transition between the liquid and gaseous states of a fluid below a predetermined value can be accurately determined, i.e., the passage of the surface of transition through a level corresponding either to the maximum predetermined filling level of the container when it is filled with fluid or to a minimum predetermined level when the container is emptied, for example, during the use of the fluid contained in it, can be accurately indicated by a characteristic signal.

These options are provided regardless of the nature of the walls of the container, in particular, even if said walls are opaque, as is the case of the metal walls of fluid cylinders with a volume on the order of one or more liters or the walls of fluid tanks, as long as the container has a predetermined and fixed orientation when the phase is determined.

Thus the phase detection method and apparatus of the invention may find numerous applications either by advantageously replacing previously known fill detection methods and devices, such as by weighing and corresponding means, for example, in order to cause the automatic cessation of the filling of a cylinder or tank upon the detection of such a signal that the level of the liquid in the cylinder or tank has reached a certain predetermined level, or by enabling the determination of the fill level under conditions where such determination has not been normally possible, for example, in order to detect, during the use of the fluid in a cylinder or tank, that the cylinder or tank will soon be empty and must be changed or recharged and to trigger upon the receipt of said signal an appropriate alarm or automatic transfer of the user being supplied to a full cylinder or tank, respectively.

In particular, the present invention proposes a method for transferring fluid from a source container to a receiving container, characterized in that the transfer is carried out under conditions such that the fluid becomes liquid in the receiving container, where a certain maximum level of the fluid in the liquid phase is defined, the phase of the fluid is determined, as the fluid is transferred, at that level by the phase-determining method of the invention and the transfer is stopped when liquid is detected at the predetermined maximum level.

The transfer can be terminated manually, i.e., by the action of an operator upon detection of an alarm caused by the receipt of said signal, or automatically if a method is implemented using a transfer means according to the invention characterized in that it comprises means for introducing the fluid as a liquid into the receiving container, a phase determination means according to the invention to determine the phase of the fluid at a certain level of the receiving container as the fluid is being transferred, and means to stop the transfer upon receipt of a characteristic signal indicating that liquid has reached the determined level in the receiving container.

As a result, the fill level of the receiving container cannot exceed a predetermined value, dictated, for example, by safety considerations.

In addition, means traditionally used for this purpose can be provided, such as weighing of the receiving container during filling, with the same effect of terminating the transfer when the weight of said container and its contents exceeds a certain predetermined value, in a manner well known to one skilled in the art.

The fluid is preferably sampled in the receiving container in order to detect the phase of the fluid at a certain level under conditions that compensate for the gradual filling of the receiving container with liquid fluid, while sampling the fluid as a gas.

For this purpose, the procedure is different depending on whether the fluid is sampled as a gas or a liquid in the source container in order to transfer and introduce it in the receiving container as a liquid.

If the fluid is sampled as a gas in the source container, in practice in an upper zone of said container, the method of the invention can be advantageously implemented by withdrawing in parallel a relatively high flow of gaseous fluid from the source container and a relatively small flow of gaseous fluid gas from the predetermined level in the receiving container passing the fluid through depressurizing means, measuring the temperature of the fluid from the receiving container after depressurization in order to carry out the phase determination of the invention and then liquefying the gaseous fluid thus withdrawn and introducing it as a liquid into the receiving container.

For this purpose, the transfer apparatus of the invention is characterized in that the means for introducing the liquid into the receiving container includes means for withdrawing, in parallel, a relatively high flow of gaseous fluid from the source container and a relatively small flow of gaseous fluid from the receiving container at the predetermined level of the latter as well as an apparatus for depressurizing and measuring the temperature of the fluid from the receiving container after depressurization, forming part of the phase determination device of the invention, as well as for liquefying the gas thus withdrawn before introducing it into the receiving container.

Note that, as is well known, the transfer can be entirely carried out by withdrawing gaseous fluid from the source container, or by first withdrawing liquid fluid from the source container, allowing an increased flow rate and then completing the transfer by withdrawing gaseous fluid from the source container.

In the latter case, the liquid fluid is transferred by withdrawing gaseous fluid from the receiving container at the predetermined level and using the means for measuring the temperature of the fluid after depressurization for implementing the phase determination method of the invention by liquefying the gas thus withdrawn and introducing it as a liquid into the source container. When the flow of the liquid becomes zero, the transfer of the liquid is stopped and replaced by withdrawing the fluid as a gas from the source container under the conditions previously indicated for such a transfer.

For this purpose, the transfer means of the invention is characterized in that the means for introducing the liquid fluid into the receiving container comprises means for communicating between the lower zones of the source container and the receiving container, respectively, in order to allow direct transfer of the liquid fluid to be effected and means for withdrawing the gaseous fluid into the receiving container at the level of the latter, and through the depressurizing means and the means for measuring the temperature of the pressurized gas from the receiving container after depressurization, as well as for liquefying the gas thus withdrawn before introducing it in the source container. Furthermore, the device preferably comprises means for detecting the interruption of liquid flow during transfer and to control the shutdown of the means for withdrawing the pressurized gas into the receiving container or, possibly the switching from the direct transfer of liquid fluid to transfer by withdrawing in parallel with such flows of gaseous fluid.

Other characteristics and advantages of the methods and apparatus for determining the phase of a fluid and for the transfer of the fluid will become evident from the following description of a non-restrictive embodiment, as well as from the attached drawings that are an integral part of this description.

BRIEF DESCRIPTION OF THE DRAWINGS

FIGS. 2 and 3 illustrate the same installation in its modes corresponding to the recovery of the refrigerant in gaseous and liquid phases, respectively, as it leaves the refrigeration apparatus.

DESCRIPTION OF THE PREFERRED EMBODIMENTS

Figure 1:
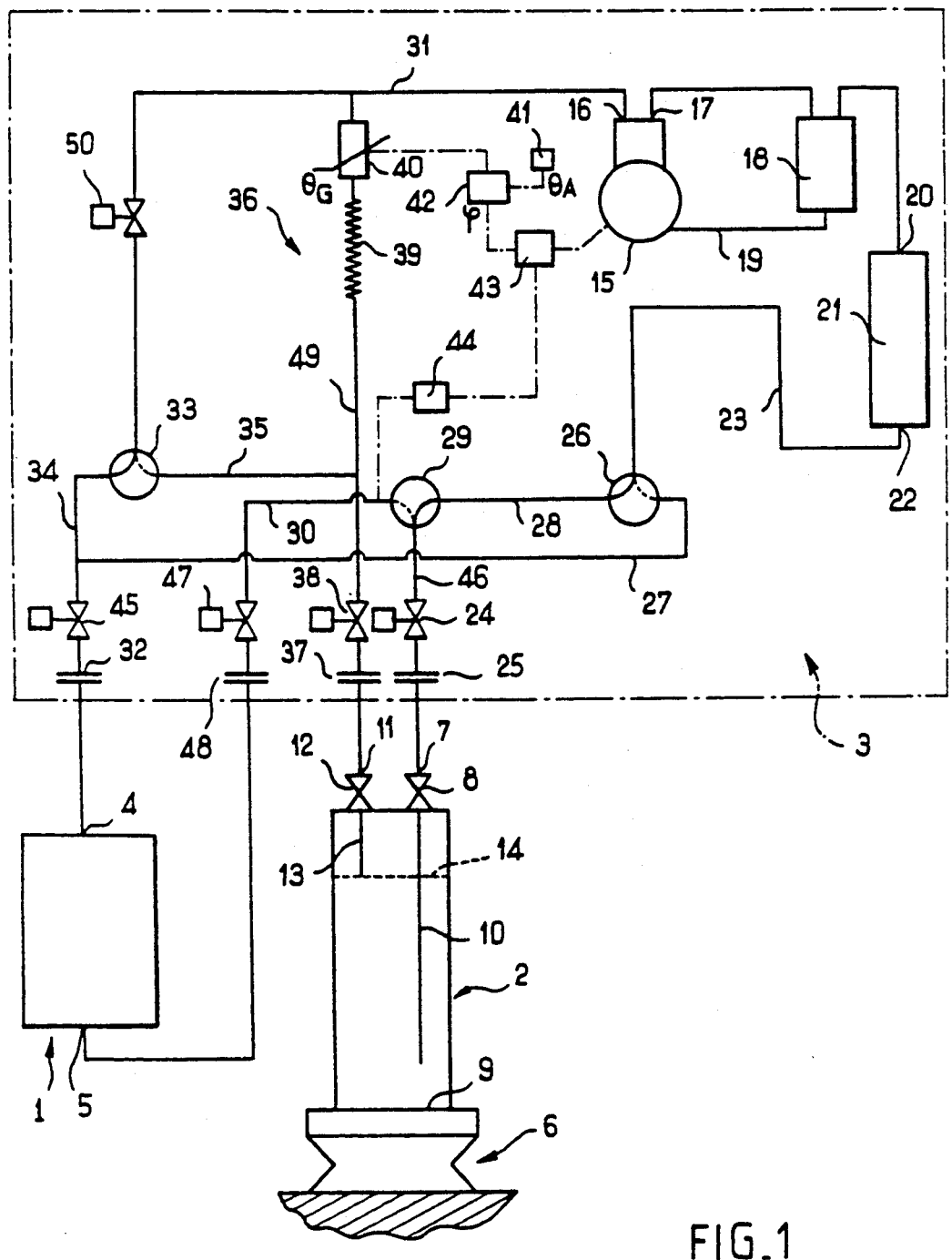
FIG. 1 depicts schematically an installation embodying different aspects of the invention within the framework of the recovery of a refrigerant from a refrigeration apparatus by transfer to a storage cylinder.

Of course, although the method and apparatus of the invention for determining the phase of a fluid, as well as the method and device of the invention for transferring a fluid are thus described in reference to the example of transfer of a refrigerant from a refrigeration apparatus to a refrigerant storage cylinder, one skilled in the art will easily understand that the methods and apparatus of the invention may be used in other applications and will make the adaptations required by each case to the arrangements described herein without, however, departing from the framework of the present invention.

In all figures, 1 denotes the refrigerant circuit for emptying a refrigeration apparatus, not shown, and 2 denotes a storage cylinder for the refrigerant. Circuit 1 and cylinder 2, both hermetically sealed, constitute a source container and a receiving container for the refrigerant, respectively. The refrigerant is transferred from one to the other by transfer unit 3.

It is known that in refrigerant circuit 1 of a refrigeration apparatus the refrigerant, consisting, for example, of a mixture of fluids known under the registered trademark "Freon," changes between a liquid and a gas, refrigerant in these two phases always being present within circuit 1.

In order to allow the transfer of the refrigerant, both as a gas and as a liquid, respectively, from circuit 1, the circuit has, in the example illustrated, gas outlet connection 4 in an upper zone of circuit 1 and liquid outlet connection 5 in the lower zone of circuit 1. "Upper zone" and "lower zone" of circuit 1 are defined as zones that, under normal conditions of use of the refrigeration apparatus or after its preparation for transfer of the refrigerant are located at the top of a component such as the compressor outlet of circuit 1 containing the refrigerant in a gaseous state and on the bottom of a component, such as a condenser or a liquid line upstream from an expansion valve of circuit 1 containing the refrigerant in a liquid state.

Connections 4 and 5 can be installed at the time that the refrigerant is to be transferred from circuit 1 or they can pre-exist, in which case they are hermetically sealed, for example with plugs, when a transfer is not taking place, in particular when the refrigeration apparatus is in operation.

Note that if the refrigerant in circuit 1 can be withdrawn for transfer into cylinder 2 as a gas only, liquid outlet connection 5 can be omitted or, if it exists, remain inoperative and closed.

In order to always receive the refrigerant as a liquid, cylinder 2, which can advantageously rest on weighing means 6 of a well-known type that allows the level of fill to be estimated by weighing, has, in an upper zone, liquid inlet connection 7, which connection is provided with stop valve 8 and, extending downward into cylinder 2 to near the bottom 9 of the cylinder, immersion tube 10. Cylinder 2 also has, in its upper zone, gas outlet connection 11, which connection is provided with stop valve 12 and, extending downward into cylinder 2, immersion tube 13 which, however, ends at predetermined level 14 which level is considerably higher than the level at which immersion tube 10 ends. Level 14 is the predetermined maximum level of liquid refrigerant in cylinder 2, it being understood that gaseous refrigerant occupies the upper zone of cylinder 2 when liquid refrigerant is introduced into the cylinder 2 and more specifically, into a lower zone of the same, through immersion tube 10.

The concepts of upper and lower zones of cylinder 2, as well as the predetermined maximum liquid level in cylinder 2, refer to a predetermined orientation of the cylinder during the entire transfer operation.

Connections 11 and 7, as well as connections 4 and 5, can be of any known, removable type, e.g. of the standard threaded type.

In order to ensure the transfer of refrigerant from circuit 1 to cylinder 2, transfer unit 3 operates in the following manner, which is partially characteristic of different aspects of the present invention.

Transfer unit 3, suitable for handling gaseous refrigerant, particularly in circuit 1 and to re-liquefy it in cylinder 2, has compressor 15, with suction 16 and discharge 17 for gaseous refrigerant, at low pressure and high pressure, respectively. Discharge 17 is connected, via oil separator 18, having oil return 19 to compressor 15, to inlet 20 of condenser 21, which also has outlet 22 for condensed, i.e. liquid, refrigerant.

Pipe 23 is connected to condenser outlet 22, which pipe 23 leads to selector valve 26, and which valve can be manually operated to select either withdrawing gaseous refrigerant from circuit 1 or withdrawing liquid refrigerant from the circuit.

Selector valve 26 allows pipe 23 to be connected either in the manner illustrated in FIG. 3 and, in dotted lines, on FIG. 1, to pipe 27 leading to gas outlet connection 4 from circuit 1 and having, successively, from distributing valve 26, solenoid stop valve 45 and manual stop valve 32 either in the manner illustrated in FIG. 2 and, in solid lines, in FIG. 1, to pipe 28 leading to manual selector valve 29, for selecting the removal of either gaseous or liquid refrigerant, from circuit 1.

Valve 29 allows either pipe 28, according to an arrangement illustrated in FIG. 2 and in solid lines in FIG. 1, or pipe 30 to be connected to liquid outlet connection 5 of circuit 1. Pipe 30 has, successively from valve 29, solenoid stop valve 47 and manual stop valve 48. Pipe 46, leading to liquid inlet connection 7 of cylinder 2 has, successively from valve 29, solenoid stop valve 24 and manual stop valve 25, in a manner illustrated in FIG. 3 and in dotted lines in FIG. 1.

Suction 16 of compressor 15 is in turn connected to pipe 31 that leads, preferably through solenoid stop valve 50 to manually operated selector valve 33. Valve 33 allows pipe 31 to be connected either to pipe 34 branching out from pipe 27 between solenoid stop valve 45 and manual stop valve 26, as illustrated in FIG. 2 and in solid lines in FIG. 1, or to pipe 35 branching out from pipe 49. Pipe 49 connects gas outlet connection 11 of cylinder 2 to a zone of pipe 31 located between solenoid stop valve 50 or, when valve 50 is not present, selector valve 33, on the one hand, and suction 16 of compressor 15 on the other hand. Pipe 49 has, successively, from the connection of pipe 35 to connection 11, solenoid stop valve 38 or manual stop valve 37, as illustrated in dotted lines in FIGS. 1 and 3.

Manual stop valves 25, 32, 37 and 48 are inlet or outlet valves of transfer device 3 and are connected to connections 7, 4, 11 and 5, respectively, of cylinder 2 or of circuit 1 for transfer, preferably through flexible sections of pipes 46, 47, 49 and 30, respectively.

In order to practice the present invention, located between the connection of pipe 35 to pipe 49 and the connection of pipe 49 to pipe 31, and mounted in series in pipe 49, is device 36 for determining the phase of a fluid, in this case a refrigerant, at level 14 within cylinder 2. Device 36, a feature of the present invention, is described below.

From the connection of pipe 35 to pipe 49 to the connection of pipe 49 with pipe 31, device 36 has, successively, pressure reducing capillary 39 and thermostatic chamber 40 with adjustable temperature detection means adjusted in a manner that is easily determined by one skilled in the art for operation as described below, basically with reference to FIGS. 2 and 3. In those figures, selector valves 26 and 29 are represented as two different permanent connections. As well, selector valve 33 is represented as a permanent connection between pipes 32 and 34 and closing pipe 35, which corresponds to its position illustrated in solid lines in FIG. 1, has been omitted for clarity.

Before a transfer, respective pipes 27, 30, 46, and 49 of transfer unit 3 connected to gas outlet connection 4 of circuit 1, to its liquid outlet connection 5 and to liquid inlet and gas outlet connections 7 and 11, respectively, of gas cylinder 2 and initially shut valves 8 and 12 are opened. Then transfer unit 3 and cylinder 2 are purged if necessary under conditions that are easily determined by a person skilled in the art, preferentially by circulating fluid from circuit 1, under the effect of its pressure only, sequentially actuating the manual and solenoid valves of transfer unit 3 and actuating a vent, for example at connection 11 of cylinder 2, which can be temporarily slightly loosened for this purpose.

After purging and shutting the vent, the transfer is preferentially accomplished in two sequential steps. In a first step, the transfer is effected by withdrawing liquid refrigerant from circuit 1 through connection 5, transfer unit 3 being connected, in this case, as illustrated in FIG. 3, i.e., according to the positions of selector valves 26 and 29, illustrated in dotted lines in FIG. 1, while selector valve 33 may be in either position as described below. In a second step, transfer is accomplished by withdrawing gaseous refrigerant from circuit 1 through connection 4, the connections in this case being as indicated in FIG. 2 and, regarding valves 26, 29 and 33, represented in solid lines in FIG. 1. In both cases, liquid refrigerant comes from cylinder 2. Accomplishing the transfer by withdrawing liquid refrigerant from circuit 1 allows the transfer time to be shortened but a complete transfer can also be accomplished by withdrawing gaseous refrigerant from circuit 1, in which case transfer unit 3 and its connections can be simplified by omitting pipes 27, 30 and 35 and replacing valves 26, 29 and 33 with direct connections between pipe 23, pipe 28 and pipe 46, as well as between pipe 31, now without solenoid stop valve 50, and pipe 34. In this case, liquid outlet connection 5 does not have to be provided in circuit 1 or, if such a connection exists, it remains permanently shut.

One skilled in the art may easily find the conditions under which such a transfer is accomplished by withdrawing only gaseous refrigerant from circuit 1, from the following description of the preferred mode of transfer, including sequentially withdrawing liquid refrigerant from circuit 1, then withdrawing gaseous refrigerant from that circuit.

Refer first to FIG. 3, which illustrates transfer by withdrawing liquid refrigerant from circuit 1.

It should be remembered that, for this transfer, the now communicating pipes 30 and 46 connect liquid outlet connection 5 of circuit 1 to open liquid inlet valve 8 of cylinder 2. Manual stop valve 48 and solenoid stop valve 47 in pipe 30 are open for this purpose, as are solenoid stop valve 24 and manual stop valve 25 in pipe 46. Solenoid stop valve 50 is shut in order to isolate pipe 31 from pipes 34 and 35, the latter being already isolated from pipe 31 due to the positioning of selector valve 33. Open manual stop valves 37 and 38 in pipe 49 connect capillary 39 of device 36 to open gas outlet valve 12 of cylinder 2. Suction 16 of compressor 15 is connected to immersion tube 13 in cylinder 2 via device 36. Open manual stop valves 45 and 31 in pipe 27, now communicating with pipe 23, connect liquid outlet 22 of condenser 21 to gas outlet connection 4 of circuit 1, which open connection 4 now constitutes a liquid inlet connection.

Cylinder 2 is assumed to be initially empty of refrigerant, in particular, liquid refrigerant. Compressor 15 is started and creates a vacuum in cylinder 2 via device 36, which creates a pressure difference between the inside of cylinder 2 and the interior of circuit 1, causing liquid refrigerant to flow from circuit 1 to cylinder 2, where part of the refrigerant thus introduced vaporizes. Thus, compressor 15 withdraws, via device 36, some gaseous refrigerant, compressing and then discharging it through condenser 21, in circuit 3, where the refrigerant condenses to liquid, but immediately vaporizes by depressurization in order to preserve the equilibrium between the liquid and gaseous phases in circuit 1, at least until there is no more liquid refrigerant within circuit 1. Suitable detection means 44, known to one skilled in the art, detects the absence of liquid flow in pipe 30 and causes compressor 15 to stop by acting on compressor controller 43, also known to one skilled in the art. Then the transfer stops, unless it had previously been stopped for one of the following reasons:

due to the detection by weighing means 6 that a threshold weight of cylinder 2 and its contents has been exceeded, causing automatic shutdown of compressor 15 by controller 43; or due to the fact that liquid has reached level 14 in cylinder 2, which is detected by device 36, causing automatic shutdown of compressor 15 by controller 43;

The phase of the refrigerant at level 14 is determined by device 36 in the following manner.

When the refrigerant is a gas at level 14, this refrigerant is depressurized somewhat when traversing capillary 39, but this depressurization is not manifested in any substantial temperature drop, and, in thermostatic chamber 40, the temperature detection means detects a temperature $\theta_G$ of the refrigerant approximately identical to that of the refrigerant within cylinder 2, i.e., a temperature approximately equal to ambient temperature $\theta_A$.

If, however, liquid has reached level 14 in cylinder 2, it is liquid refrigerant that flows through capillary 39. The depressurization of this liquid refrigerant is manifested in vaporization, which in turn is manifested in a substantial temperature drop in relation to the temperature of the refrigerant within cylinder 2 prior to depressurization, or to the ambient temperature $\theta_A$. Thus, in order to prevent the liquid level in cylinder 2 from exceeding the predetermined maximum level 14, i.e., on the one hand, to prevent cylinder 2 from overfilling and, on the other hand, to prevent liquid refrigerant from reaching suction 16 of compressor 15, risking damage to the compressor. The detection, at thermostatic chamber 40, of a temperature $\theta_G$ that is substantially lower than the temperature of the refrigerant in cylinder 2, which should also be ambient temperature $\theta_A$, 0 causes compressor 15 to shut down automatically.

For this purpose, device 36 has, in the example illustrated, not only capillary 39 and thermostatic chamber 40, but also ambient temperature probe 41. Probe 41 could be replaced with a temperature probe placed in cylinder 2 but ambient temperature is, in general, an adequate indicator of the temperature within the cylinder. Device 36 also has means 42, known to one skilled in the art, for comparing temperature $\theta_G$ of the refrigerant measured by the temperature detection means in thermostatic chamber 40 and ambient temperature $\theta_A$ measured by probe 41 and for sending a signal $\phi$, characteristic of the result of this comparison, to controller 43 that controls the operation of compressor 15 by enabling compressor operation when the temperatures are approximately the same and by causing compressor 15 to stop if temperature $\theta_G$, as measured by the thermostat of thermostatic chamber 40, drops considerably below ambient temperature $\theta_A$, measured by probe 41.

In an embodiment that is within the ability of one skilled in the art, one may select a convenient reference temperature that is below any probable value of the temperature of the refrigerant in cylinder 2. When temperature $\theta_G$ of the refrigerant after depressurization drops below this reference temperature, it signals without ambiguity that the refrigerant was in a liquid state before depressurization. Taking into account operating conditions, this reference temperature can be used instead of ambient temperature $\theta_A$ or the effective temperature of the refrigerant in cylinder 2. Temperature probe 41 is then replaced with (preferably adjustable) means for setting the selected reference temperature at which comparator 42 compares temperature $\theta_G$ of the refrigerant measured in thermostatic chamber 40 to send the signal $\phi$ to comparator 43 in order to enable the operation of compressor 15 when temperature $\theta_G$ is higher than the reference temperature, indicating that it has remained near the temperature of the refrigerant prior to depressurization, in cylinder 2, or the ambient temperature, i.e., that the refrigerant being withdrawn from cylinder 2 is a gas, and to cause compressor 15 to shut down when temperature $\theta_G$ drops below the reference temperature, indicating that it is substantially lower than the temperature of the refrigerant in cylinder 2 or to the ambient temperature and that the refrigerant withdrawn from cylinder 2 is a liquid before its depressurization in capillary 39.

Controller 43, also associated with weighing means 6, stops compressor 15 when the weight of cylinder 2 and its contents exceeds a predetermined threshold. The controller, at the same time it stops compressor 15, causes solenoid stop valves 24, 38, 45 and 47 to shut. Then manual stop valves 25, 32, 37 and 48 are shut, as well as liquid outlet connection 5 of circuit 1, and valves 8 and 12 of cylinder 2 are shut, while cylinder 2 is replaced by another cylinder in order to effect the transfer either of liquid if any liquid remains in circuit 1, as described in reference to FIG. 3 or gas if there is no more liquid in circuit 1.

Note that, if there is no liquid in circuit 1 during the filling of cylinder 2, as detected by detection means 44, valves 26 and 29 can be repositioned, in a manner known to one skilled in the art, to an alignment appropriate to withdrawing gaseous refrigerant from circuit 1, as well as repositioning solenoid stop valves 24, 37, 45 and 47 as described above without stopping compressor 15.

For a transfer by withdrawing gas, as shown in FIG. 2, to which reference is now made, pipe 31 is connected in parallel, on the one hand, through open solenoid stop valve 50, to pipe 34, which in turn is connected, through solenoid stop valve 45 and similarly open valve 32 to circuit 1 via gas outlet connection 4 and, on the other hand, to immersion tube 13 of cylinder 2, through open valve 12 and via phase detection device 36 through valves 37 and 38 of pipe 49, which are open. Pipe 23 is in turn connected via pipe 28 and pipe 46 through open valves 24 and 25 of the same to open liquid inlet valve 8 into cylinder 2, the inside of which is thus connected to liquid outlet 22 of condenser 21. Pipe 30, which does not exist unless an initial transfer by withdrawing liquid refrigerant from circuit 1 is provided, is isolated not only because of the positioning of selector valve 29, but also because valves 47 and 48 are shut and liquid outlet connection 5 is closed.

To effect the transfer, the liquid level in cylinder 2, is assumed to be lower than the predetermined maximum level 14 and the weight of cylinder 2 and its contents is assumed to be less than the predetermined threshold that can be detected by weighing means 6. Compressor 15 draws, through suction 16, a relatively high flow of gaseous refrigerant from circuit 1 and a relatively low flow, due to the presence of capillary 39, of gaseous refrigerant from that present in cylinder 2, as the case may be, after a transient startup period.

The refrigerant coming to pipe 31, mostly from circuit 1, and a smaller part from cylinder 2, is compressed by compressor 15, has oil removed by oil separator 18 and then is condensed by condenser 21 before flowing, as a liquid, into cylinder 2 through immersion tube 10.

The flow of gaseous refrigerant withdrawn through outlet 11 of cylinder 2 compensates for the liquid refrigerant flowing into the cylinder through inlet 7, and can be on the order of 3 percent of the latter. However, this figure is only indicated as a non-limitative example.

The transfer can continue until circuit 1 is empty of refrigerant or until weighing means 6 detects that a predetermined threshold weight of cylinder 2 and its contents has been exceeded, or until device 36 detects that the level of liquid has reached level 14 within cylinder 2, under the conditions indicated in relation to FIG. 3.

The detection of any of these phenomena by means the implementation of which is within the ability of one skilled in the art or by device 36, as the case may be, immediately causes compressor 15 to stop and solenoid stop valves 24, 38, 45 and 50 to shut. Valves 25, 32 and 37, as well as valves 8 and 12 of cylinder 2 are then manually shut, then both cylinder 2 and circuit 1 are disconnected from transfer unit 3.

Note that pipe 35, i.e. the connection between pipe 31 and pipe 49, normally connected to gas outlet valve 12 of cylinder 2, remains inoperative when either liquid or gaseous refrigerant is transferred as described above, which corresponds to a mode of operation during which device 36 advantageously acts as a safety device, protecting cylinder 2 against overfilling, which would create an overpressure within the cylinder, on the one hand, and protecting compressor 15 from liquid refrigerant reaching its suction 16.

However, when liquid refrigerant is withdrawn from circuit 1, i.e. under the conditions indicated in reference to FIG. 3, device 36 can be bypassed by placing selector valve 33 in the position illustrated by the dotted lines in FIG. 1. In this position, selector valve 33 isolates valve 32 of pipe 31 from pipe 34, but connects pipe 31 to pipe 35 and, through the latter, to gas outlet valve 12 of cylinder 2. By opening solenoid stop valve 50, as schematically indicated by the dotted lines in FIG. 3, pipe 34 is closed off due to the positioning of selector valve 33. Then, compressor 15 withdraws gaseous refrigerant from cylinder 2 preferably through pipe 35 and only a smaller proportion through device 36, capillary 39 of which causes a pressure drop of the refrigerant that is substantially greater than that caused by passage through pipe 35. This allows a higher suction flow of the refrigerant and thus a higher transfer flow from circuit 1 to cylinder 2, in comparison to the mode of operation described previously with reference to PIG. 3, but has the inconvenience of considerably reducing the effectiveness of device 36. Thus, for reasons of safety, it is preferable to proceed in this manner only during the initial phase of withdrawing liquid refrigerant from circuit 1. Then, changeover to the mode of operation described in reference to FIG. 3 is accomplished by shutting solenoid stop valve 50 and, possibly, repositioning selector valve 33 for operation according to the mode described with reference to FIG. 2.

One skilled in the art will easily understand that the embodiment of the methods and apparatus of the invention described herein is only a non-limitative example, allowing the application and operation of the device to determine the phase of a fluid to be illustrated and that such detection may be applied just as advantageously in other contexts where it can be implemented with means different from device 36 described and illustrated above. The adaptation of the arrangements described for each particular case is within the ability of one skilled in the art.

I claim:

1. A method of determining whether fluid at a predetermined level (14) of a fluid storage container (2) is a liquid or a gas comprising the steps of:
   withdrawing a sample of said fluid from said container at said level;
   depressurizing said sample under conditions such that said fluid will become a gas if it is a liquid before such depressurization;
   measuring the temperature ($\theta_G$) of said fluid after depressurization;
   establishing a reference temperature ($\theta_A$) as a function of the temperature of said fluid in said container;
   comparing said fluid temperature and said reference temperature;
   concluding that said fluid is a gas or a liquid from the results of said comparing step based on the following criteria—
      if said fluid temperature and said reference temperature are approximately equal, then said fluid is a gas at said level of said container but
      if said fluid temperature is substantially lower than reference temperature, then said fluid is a liquid at said level of said container.

2. The method of claim 1, further characterized in that said temperature establishing step includes the substep of
   selecting said reference temperature from a group of temperatures that includes
      ambient temperature and
      the temperature of said fluid in said container.

3. An apparatus (36) for determining whether a fluid at a predetermined level (14) of a fluid storage container (2) is a liquid or a gas comprising:
   means (13, 49) for withdrawing said fluid from said container at said predetermined level;
   means (39), in downstream fluid flow relationship with said withdrawing means, for depressurizing said fluid such that said fluid will become a gas if it is a liquid prior to said depressurization;
   means (40), in downstream fluid flow relationship with said depressurizing means, for measuring the temperature of said fluid after depressurization;
   means (41) for establishing a reference temperature $\theta_A$; and
   means (42) for comparing said fluid temperature and said reference temperature and producing a signal $\phi$ that is characteristic of the result of this comparison.

4. The apparatus of claim 3 further characterized in that said means for establishing said reference temperature is chosen from a group that includes
   means for measuring ambient temperature and
   means for measuring the temperature of said fluid in said container.

5. A method of transferring a fluid from a source container (1) to a receiving container (2) until the level of said fluid in the liquid state reaches a predetermined level (14) in said receiving container comprising the steps of:
   transferring said fluid under conditions such that said fluid enters said receiving container as liquid;
   withdrawing a sample of said fluid from said container at said predetermined level;
   depressurizing said sample under conditions such that said fluid will become a gas if it is a liquid before depressurization;
   measuring the temperature ($\theta_G$) of said fluid after depressurization;
   establishing a reference temperature ($\theta_A$) as a function of the temperature of said fluid in said container;
   comparing said fluid temperature and said reference temperature;
   concluding that said fluid is a gas or a liquid from the results of said comparing step based on the following criteria—
      if said fluid temperature and said reference temperature are approximately equal then said fluid is a gas at said predetermined level of said receiving container but
      if said fluid temperature is substantially lower than said reference temperature then said fluid is a liquid at said predetermined level of said receiving container;
   terminating said transfer when the level of liquid in said receiving container is at said predetermined level.

6. The method of claim 5 in which said withdrawing step includes withdrawing said fluid under conditions such that withdrawing said fluid as a gas from said receiving container compensates for the fill of said receiving container with said fluid as a liquid.

7. The method of claim 6 in which said transferring step includes the substeps of:
   withdrawing in parallel a relatively high flow of gaseous fluid from said source container and a relatively low flow of gaseous fluid from said predetermined level in said receiving container (2) level;
   passing said gaseous fluid through depressurization means (39) and means (40) for measuring said fluid temperature of said fluid from said receiving container after depressurization
   liquefying said gaseous fluid thus withdrawn; and
   introducing said fluid as a liquid into said receiving container.

8. The method of claim 6 in which said transferring step includes the substeps of:
   withdrawing said fluid as a gas from said predetermined level of said receiving container;

passing said fluid through said depressurization means and said means for measuring said fluid temperature after depressurization;

liquefying said gaseous fluid thus withdrawn; and introducing said fluid as a liquid into said source container.

9. The method of claim 8, further characterized in that when the flow of said liquid fluid is reduced to zero, said fluid is transferred as a gas.

10. An apparatus (3) for transferring a fluid from a source container (1) to a receiving container (2) comprising means (15, 21) for liquefying and introducing said fluid as a liquid into said receiving container (2);

a device (36) for determining whether said fluid at a predetermined level (14) of said receiving container is a liquid or a gas as said fluid is transferred; and means (43) for terminating said transfer upon receipt of a signal $\phi$ that is characteristic of liquid having reached said predetermined level in said receiving container.

11. The apparatus of claim 10 in which said means for liquefying and introducing liquid fluid into said receiving container comprise:

means (15, 21) for withdrawing, in parallel, a relatively large proportion of said fluid as a gas from said source container and a relatively small proportion of said fluid as a gas from said predetermined level of said receiving container;

depressurizing means (39); and means (40) for measuring the temperature of said fluid after depressurization.

12. The apparatus of claim 10 in which said means for liquefying and introducing said liquid fluid into said receiving container comprise:

means (30, 10), in fluid flow communication with respective lowest zones of said source container and said receiving container, for allowing a direct transfer of said fluid as a liquid; and means (15, 21), in downstream fluid flow relationship with said means for allowing direct transfer, for withdrawing said fluid as a gas from said predetermined level of said receiving container;

means (39), in downstream fluid flow relationship with said withdrawing means, for depressurizing said fluid;

means (40), in downstream fluid flow relationship with said depressurizing means, for measuring the temperature of said fluid.

13. The apparatus of claim 12 further comprising means (44) for detecting the cessation of flow of liquid fluid and issuing a signal to shut down said withdrawing means.

14. The apparatus of claim 12 further comprising means (44) for detecting the cessation of flow of liquid fluid and issuing a signal to change from transferring fluid as a liquid to transferring by withdrawing gaseous fluid.

* * * * *